(12) United States Patent
Abe et al.

(10) Patent No.: US 8,187,825 B2
(45) Date of Patent: May 29, 2012

(54) THIOL DETECTION METHOD

(75) Inventors: Hiroshi Abe, Saitama (JP); Yoshihiro Ito, Tokyo (JP); Aya Shibata, Saitama (JP); Mika Ito, Saitama (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 12/919,299

(22) PCT Filed: Jan. 30, 2009

(86) PCT No.: PCT/JP2009/051579
§ 371 (c)(1),
(2), (4) Date: Dec. 6, 2010

(87) PCT Pub. No.: WO2009/107448
PCT Pub. Date: Sep. 3, 2009

(65) Prior Publication Data
US 2011/0111446 A1 May 12, 2011

(30) Foreign Application Priority Data
Feb. 29, 2008 (JP) .................. 2008-049464

(51) Int. Cl.
G01N 33/574 (2006.01)
C12Q 1/02 (2006.01)
A01N 55/02 (2006.01)
A01N 43/16 (2006.01)
A01N 31/14 (2006.01)

(52) U.S. Cl. ......... 435/7.23; 435/29; 514/185; 514/451; 514/721

(58) Field of Classification Search .................. None
See application file for complete search history.

(56) References Cited

U.S. PATENT DOCUMENTS
2004/0029837 A1* 2/2004 Fries et al. .................. 514/100
2006/0240455 A1 10/2006 Fries et al.
2006/0280652 A1 12/2006 Pitner et al.

FOREIGN PATENT DOCUMENTS
JP 2004-508448 3/2004
WO 2006/025887 3/2006

OTHER PUBLICATIONS

Bouffard et al. Organic Letters, 2008, vol. 10, No. 1, pp. 37-40. (published on the web Dec. 7, 2007).*
Jean Bouffard et al., "A Highly Selective Fluorescent Probe for Thiol Bioimaging", Organic Letters, 2008, vol. 10, No. 1,, pp. 37-40.
Wei Jiang et al., "A Highly Selective Fluorescent Probe for Thiophenols", Angewandte Chemie, International Edition, 2007, 46,, pp. 8445-8448.
Hatsuo Maeda et al., "2,4 Dinitrobenzenesulfonyl Fluoresceins as Fluorescent Alternatives to Ellman's Reagent in Thiol-Quantification Enzyme Assays", Angewandte Chemie, International Edition, 2005,, pp. 2922-2925.
Bo Tang, "A Rhodamine-Based Fluorescent Probe Containing a Se-N Bond for Detecting Thiols and Its Application in Living Cells", Journal of the American Chemical Society, 2007,, pp. 11666-11667.
Phani Kumar Pullela et al., "Fluorescence-based detection of thiols in vitro and in vivo using dithiol probes", Analytical Biochemistry, 2006,, pp. 265-273.
Aya Shibata et al., "Rhodamine-based fluorogenic probe for imaging biological thiol", Bioorganic & Medicinal Chemistry Letters, 2008,, pp. 2246-2249.
Mika Ito et al., "Kyukaku Chikan Hanno ni Motozuku Shinki Keiko Hassei Kagobutsu o Mochiita Seitai Bunshi no Kenshutsu", Abstracts of Symposium on Medicinal Chemistry, 27, Nov. 10, 2008, pp. 318-319.
Ellman et al., Biochem. Biophys, 1959, 82, 70.
Maeda et al., Chem. Int. Ed. 2006, 45, 1810.
Wei Jiang et al., "A Highly Selective Fluorescent Probe for Thiophenols", Angewandte Chemie,, pp. 8445-8448, 2007.
Jean Bouffard et al., "A Highly Selective Fluorescent Probe for Thiol Bioimaging", Organic Letters,, pp. 37-40, 2007.
Hatsuo Maeda, "2,4 Dinitrobenzenesulfonyl Fluoresceins as Fluorescent Alternatives to Ellman's Reagent in Thiol-Quantification Enzyme Assays", Angewandte Chemie,, pp. 2922-2925, 2005.
International Preliminary Report on Patentability for PCT/JP2009/051579, mailed Oct. 12, 2010.

* cited by examiner

Primary Examiner — Chris R Tate
Assistant Examiner — Douglas F White
(74) Attorney, Agent, or Firm — Greenblum & Bernstein, P.L.C.

(57) ABSTRACT

It is an object of the present invention to provide: a novel thiol-detecting reagent, which can be used in vivo and which solves the problem regarding the generation of background fluorescence due to hydrolysis; and a method for detecting thiol using the aforementioned reagent. The present invention provides a compound represented by the following formula (1):

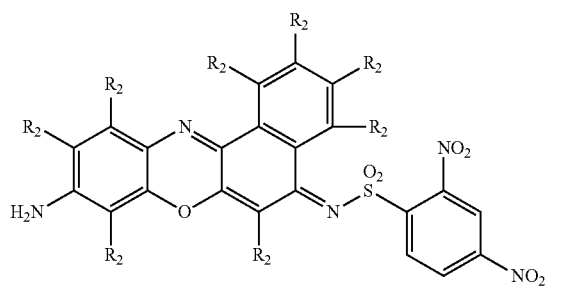

(1)

wherein each $R_2$ independently represents an alkyl group containing 1 to 6 carbon atoms, a halogen atom, or a hydrogen atom.

6 Claims, 3 Drawing Sheets

[FIGURE 1]
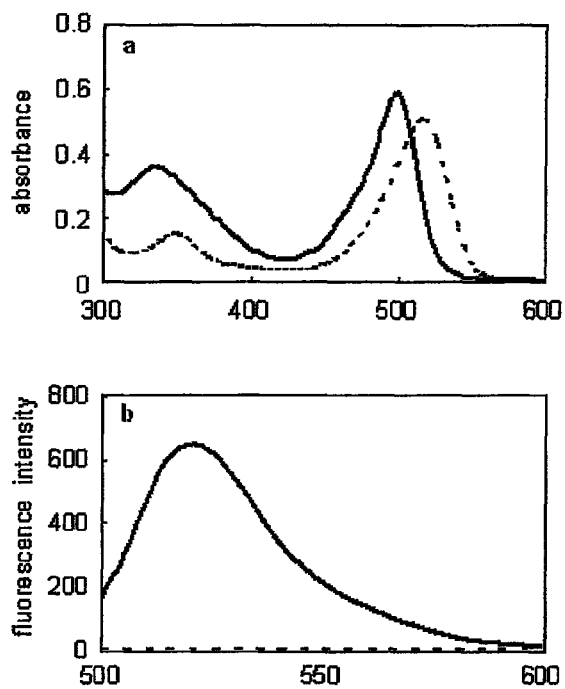
[FIGURE 2]
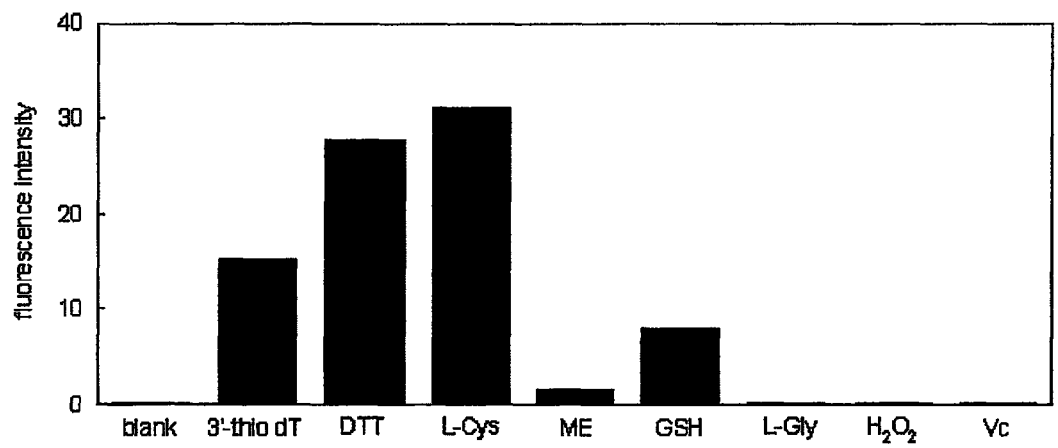

[FIGURE 3]
[FIGURE 4]
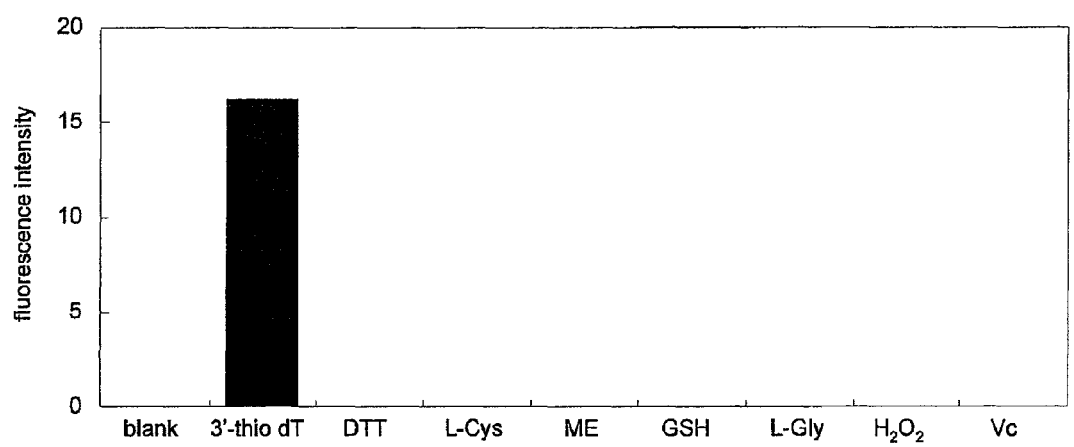
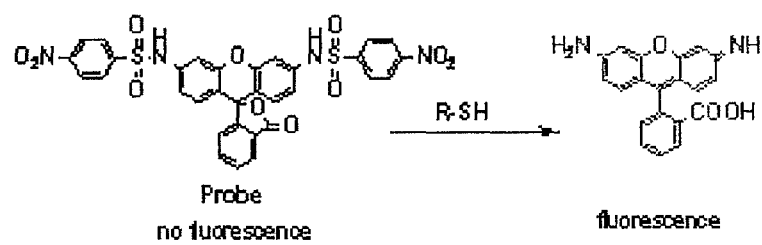

[FIGURE 5]
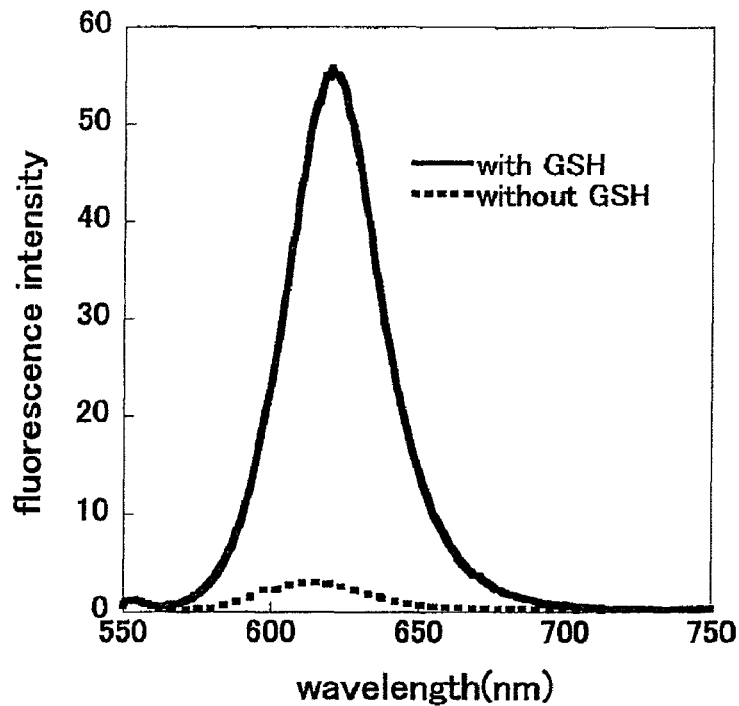
[FIGURE 6]
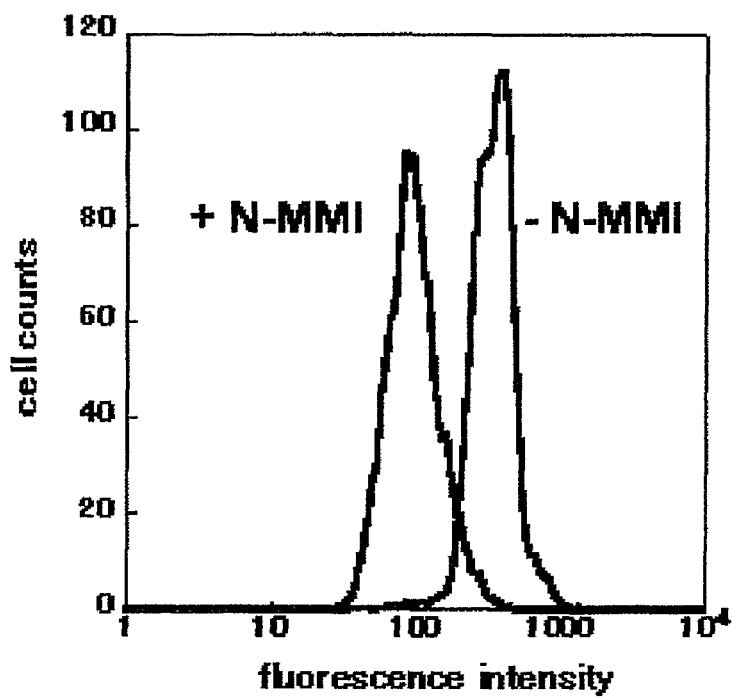

THIOL DETECTION METHOD

TECHNICAL FIELD

The present invention relates to: a novel compound capable of detecting thiol, and particularly, thiol existing in a biomolecule such as a protein; and a thiol-detecting reagent and a method for detecting thiol, in which the above-described compound is used.

BACKGROUND ART

Cellular thiol plays an important role in a biological system. A change in thiol concentration is associated with oxidation stress involved in poison and disease. Glutathione is the most abundant cellular thiol. It acts as an antioxidant on cells, so that it protects the cells from many cancerogenic substances. Homocysteine is a risk factor for diseases such as cardiovascular disease and Alzheimer's disease. A thiol group in a cysteine residue is involved in the three-dimensional structure of a protein through the formation of a disulfide bond. The absence of cysteine may cause serious health problems. Accordingly, the detection of intracellular thiol is extremely important for examining the functions of cells.

Ellman reagent is a thiol-detecting reagent, which has been broadly used from of old (Non-Patent Document 1). However, since an assay using this reagent is based on a change in absorbance, the reagent can be used only in vitro. Several methods for detecting thiol, involving a sensitive fluorescent probe, have been reported. A fluorescein derivative protected by 2,4-dinitrobenzenesulfonyl ester has been reported (Non-Patent Documents 2 and 3). This probe reacts with a biological thiol to generate a high fluorescence intensity in a short reaction time. However, this probe is problematic in that since its sulfonyl ester is hydrolyzed in an aqueous solution, background fluorescence may be generated.

Recently, a fluorescent probe having a 2,4-dinitrobenzenesulfonamide (DNB) group has been reported (Non-Patent Documents 4 and 5). A sulfonamide group is resistant to hydrolysis, and thus, no background fluorescence is generated.

Non-Patent Document 1: Ellman, G. L. Arch. Biochem. Biophys. 1959, 82, 70.
Non-Patent Document 2: Maeda, H.; Matsuno, H.; Ushida, M.; Katayama, K.; Saeki, K.; Itoh, N. Angew. Chem. Int. Ed. 2005, 44, 2922.
Non-Patent Document 3: Maeda, H.; Katayama, K.; Matsuno, H.; Uno, T. Angew. Chem. Int. Ed. 2006, 45, 1810.
Non-Patent Document 4: Jiang, W.; Fu, Q.; Fan, H.; Ho, J.; Wang, W. Angew. Chem. Int. Ed. 2007, 46, 8445.
Non-Patent Document 5: Bouffard, J.; Kim, Y.; Swager, T. M.; Weissleder, R.; Hilderbrand, S. A. Org. Lett. 2008, 10, 37.

DISCLOSURE OF THE INVENTION

Problem to be Solved by the Invention

It is an object of the present invention to provide: a novel thiol-detecting reagent, which can be used in vivo and which solves the problem regarding the generation of background fluorescence due to hydrolysis; and a method for detecting thiol using the aforementioned reagent.

Means for Solving the Problem

As a result of intensive studies directed towards achieving the aforementioned object, the present inventors have succeeded in synthesizing a novel fluorogenic compound by protecting a widely used, inexpensive rhodamine or cresyl violet by a 2,4-dinitrosulfonyl group. The fluorogenic compound of the present invention is able to specifically react with thiol, so as to generate fluorescence. As a result, the present fluorogenic compound is able to visualize thiol existing in living cells. The present invention has been completed based on these findings.

The present invention provides a compound represented by the following formula (1):

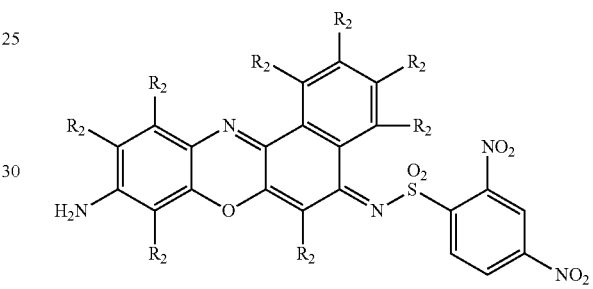

(1)

wherein each $R_2$ independently represents an alkyl group containing 1 to 6 carbon atoms, a halogen atom, or a hydrogen atom.

Preferably, there is provided a compound represented by the following formula (1A):

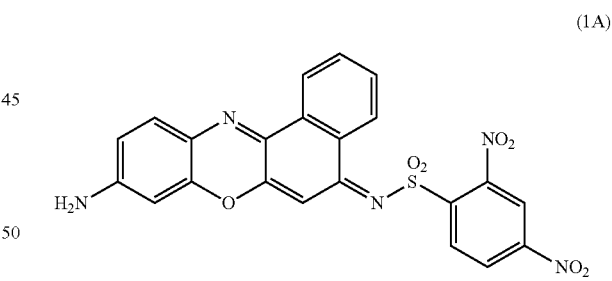

(1A)

The present invention further provides a compound represented by the following formula (2):

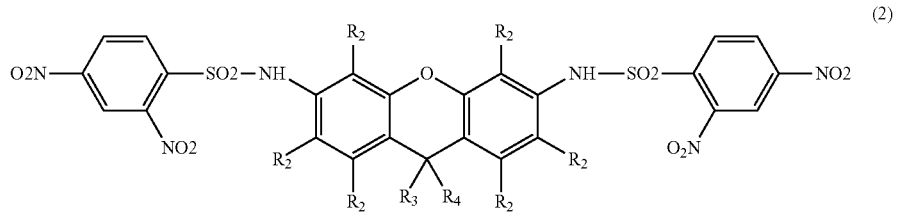

(2)

wherein each $R_2$ independently represents an alkyl group containing 1 to 6 carbon atoms, a halogen atom, or a hydrogen atom; $R_3$ represents an alkyl group containing 1 to 6 carbon atoms, an aryl group, or a hydrogen atom; $R_4$ represents a group containing an oxygen atom, or a hydrogen atom; and $R_3$ and $R_4$ may bind to each other to form a ring.

Preferably, there is provided a compound represented by the following formula (2A):

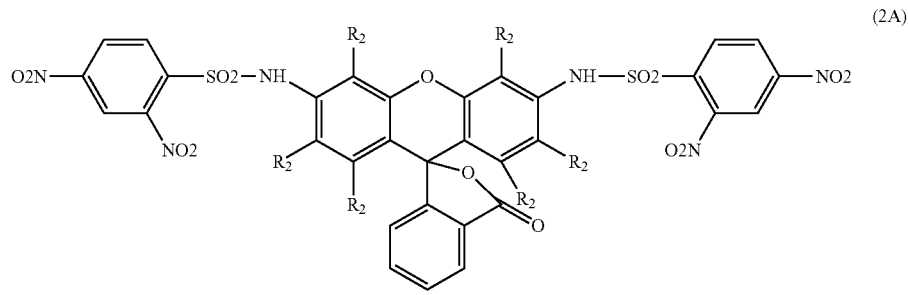

(2A)

wherein each $R_2$ independently represents an alkyl group containing 1 to 6 carbon atoms, a halogen atom, or a hydrogen atom.

Further preferably, there is provided a compound represented by the following formula (2B):

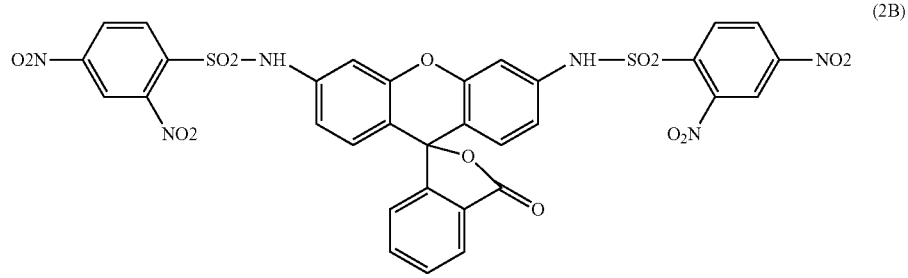

(2B)

The present invention further provides a thiol-detecting reagent which comprises the aforementioned compound of the present invention.

The present invention further provides a method for detecting thiol, which comprises detecting fluorescence which is generated by allowing the aforementioned compound of the present invention to react with a compound having a thiol group.

Preferably, the reaction of the compound of the present invention with the compound having a thiol group is carried out in a cell.

Preferably, the compound having a thiol group is a biomolecule.

Effects of the Invention

Since the fluorogenic compound of the present invention is able to specifically react with thiol to generate fluorescence, it is useful as a thiol-detecting reagent for visualizing thiol in living cells. In particular, by using a thiol-detecting reagent comprising the fluorogenic compound of the present invention, the localization of thiol in a cell can be examined.

BEST MODE FOR CARRYING OUT THE INVENTION

The embodiments of the present invention will be described in detail below.

In the present invention, a novel fluorescent probe was produced from rhodamine (Formula 2B). Since a rhodamine dye has a high fluorescence intensity and is resistant to photo bleaching (loss of photosensitivity), it is most widely used as a fluorescent labeling substance for biomolecules. There are a group of rhodamine derivatives having a light emission range from 450 to 700 nm. The fluorescent probe of the present invention can be applied to a large number of rhodamine derivatives, so as to produce a multicolor fluorescence-detecting reagent used for biological thiol.

The nucleophilic attack of a thiol group on a 2,4-dinitrobenzenesulfonamide group and the subsequent cleavage of a sulfonamide bond are involved in the chemistry of a fluorogenic probe. Thereafter, rhodamine of a ring-opening polymerized lactone type emits a fluorescence signal (Reaction Formula 1). The probe of the present invention was synthesized from commercially available rhodamine 110 in one step. A starting compound was treated with 2,4-dinitrobenzenesulfonyl chloride in the presence of KOt-Bu in DMF for 16 hours, so as to obtain a probe of interest at a yield of 10%.

Reaction Formula 1: Reaction mechanism of fluorogenic probe

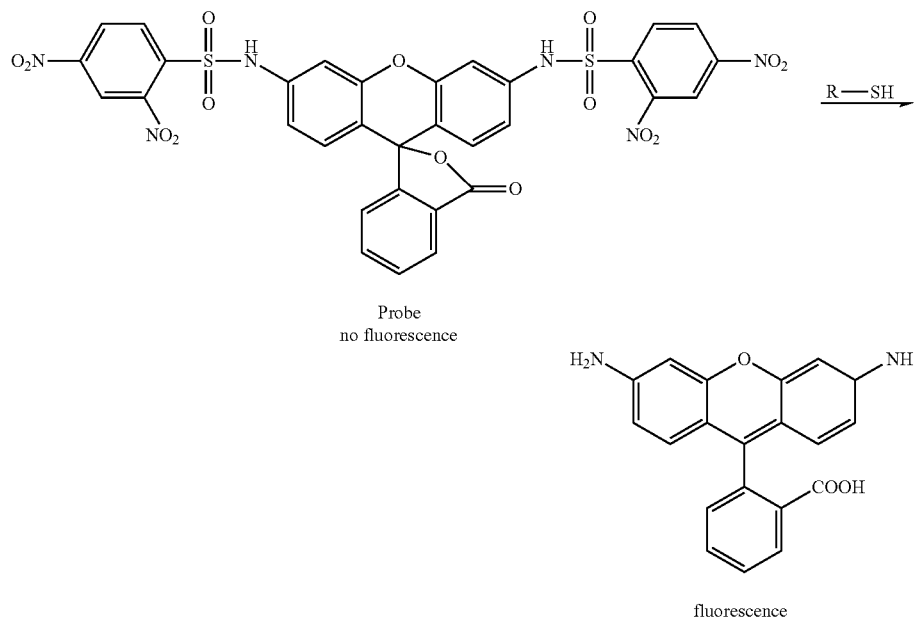

Probe
no fluorescence fluorescence

The 2,4-dinitrobenzenesulfonamide group of the probe is cleaved as a result of a reaction with thiol to generate rhodamine, so as to generate a fluorescence signal.

In the above reaction, a green fluorescent probe having rhodamine as a basic skeleton has been developed. However, in an imaging operation, fluorescence existing on a longer wavelength side, namely, a red fluorescent compound is useful. Hence, a red fluorescent probe (DNs-CV) having cresyl violet (CV) as a basic skeleton has been designed (Formula 1A). In the case of this probe, fluorescence is quenched only by protecting one amino group of CV by a dinitrobenzenesulfonyl (DNs) group. If thiol is present, DNs as a protecting group is removed by a nucleophilic substitution reaction, so that fluorescence is generated. This probe was produced by adding KOt-Bu and $ClSO_2Ph(NO_2)_2$ to cresyl violet and reacting them.

Reaction Formula 2: Reactions mechanism of fluorogenic probe

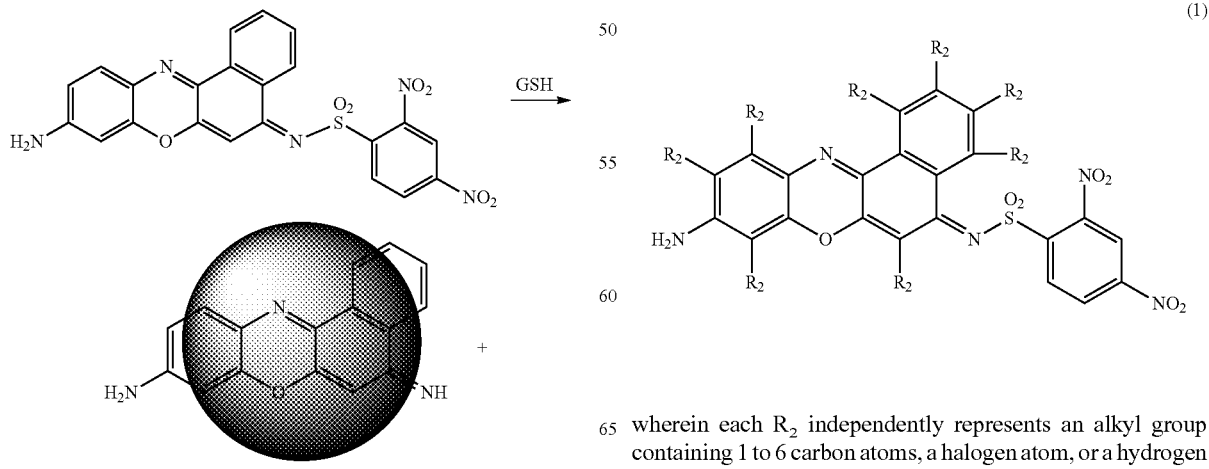

-continued

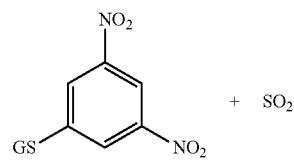

The 2,4-dinitrobenzenesulfonamide group of the probe is cleaved as a result of a reaction with thiol to generate cresyl violet, so as to generate a fluorescence signal.

The compound of the present invention is a compound represented by the following formula (1).

(1)

wherein each $R_2$ independently represents an alkyl group containing 1 to 6 carbon atoms, a halogen atom, or a hydrogen atom.

Preferably, the compound of the present invention is a compound represented by the following formula (1A):

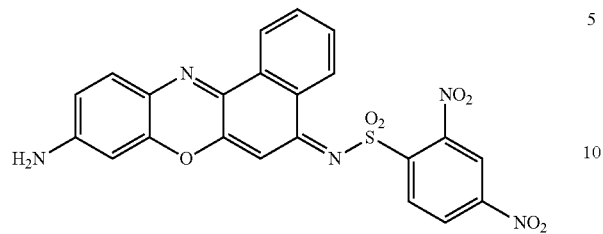

(1A)

The compound (probe) of the present invention is a compound represented by the following formula (2):

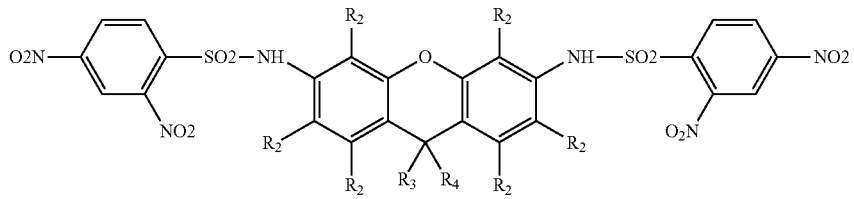

(2)

wherein each $R_2$ independently represents an alkyl group containing 1 to 6 carbon atoms, a halogen atom, or a hydrogen atom; $R_3$ represents an alkyl group containing 1 to 6 carbon atoms, an aryl group, or a hydrogen atom; $R_4$ represents a group containing an oxygen atom, or a hydrogen atom; and $R_3$ and $R_4$ may bind to each other to form a ring.

Preferably, the compound of the present invention is a compound represented by the following formula (2A) or (2B):

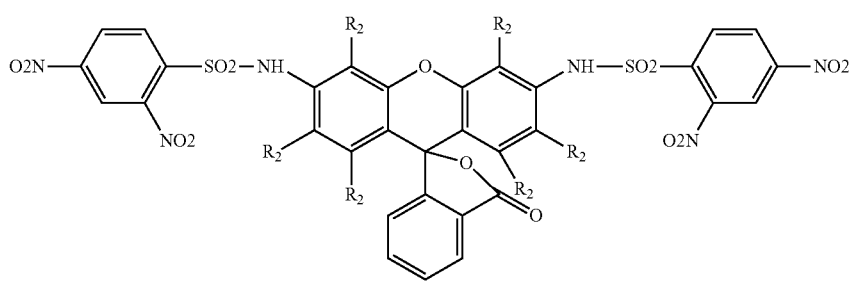

(2A)

wherein each $R_2$ independently represents an alkyl group containing 1 to 6 carbon atoms, a halogen atom, or a hydrogen atom,

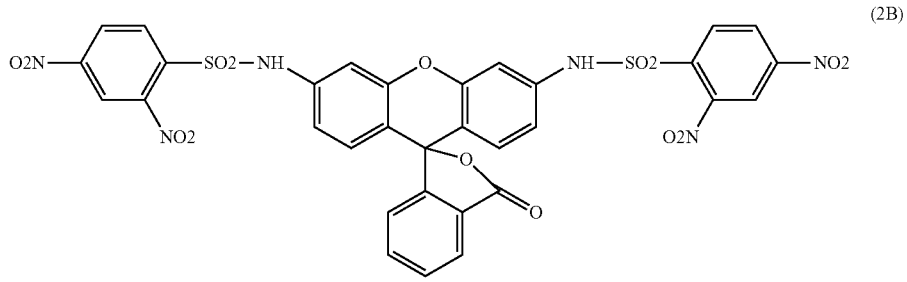

(2B)

In the present invention, either a linear or branched alkyl group may be used as an alkyl group containing 1 to 6 carbon atoms. Examples of such alkyl group include a methyl group, an ethyl group, a propyl group, a butyl group, a pentyl group, and a hexyl group.

In the present invention, examples of a halogen atom include a fluorine atom, a chlorine atom, a bromine atom, and an iodine atom.

In the present invention, examples of an aryl group include a phenyl group and a naphthyl group.

cell, for example, by incubating the cell together with the above-described compound and then obtaining the fluorescent image of the cell.

The present invention will be more specifically described in the following examples. However, these examples are not intended to limit the scope of the present invention.

EXAMPLES

Example A

Synthesis Example A1: Synthesis of the probe of the present invention

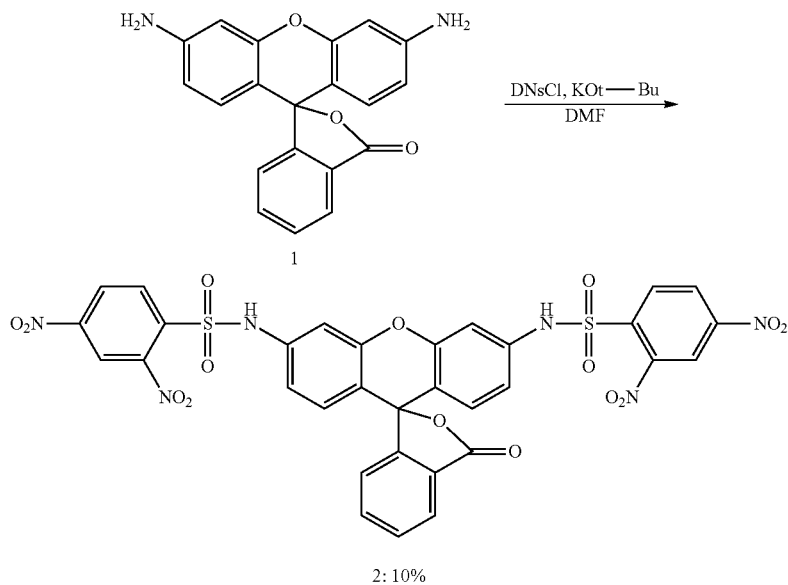

2: 10%

In the present invention, examples of a group containing an oxygen atom include —O— and —COO—.

If the compound represented by the formula (1) of the present invention (which also includes the compound represented by the formula (1A)) or the compound represented by the formula (2) of the present invention (which also includes the compound represented by the formula (2A) or (2B)) is allowed to react with a compound having a thiol group, the compound emits fluorescence as a result of the reaction represented by the above-described reaction formula 1. Accordingly, it is possible to examine the localization of thiol in a A KOt-Bu (92.2 mg, 0.82 mmol, 3 eq) solution in THF (2 ml) was added dropwise to a rhodamine 110 (110.9 mg, 0.28 mmol) solution in DMF (2 ml) at 0° C. Thirty minutes later, 2,4-dinitrobenzenesulfonyl chloride (220.2 mg, 0.83 mmol, 3 eq) was added to the reaction solution. The mixed solution was left at room temperature for 2 hours, and 2,4-dinitrobenzenesulfonyl chloride (223 mg, 0.84 mmol, 3 eq) was then added to the reaction solution. Sixteen hours later, the reaction solution was diluted with ethyl acetate, followed by liquid separation using a saturated $NaHCO_3$ aqueous solution. The organic layer was dried over $Na_2SO_4$, and the resultant was then subjected to vacuum concentration. The residue was purified by flash column chromatography, so as to obtain the above-described compound 2 (20.7 mg, 0.03 mmol, 10%).

$^1$H-NMR (400 MHz, CDCl$_3$/CD$_3$OD): δ 8.47-8.46 (d, 2H, J=2.2), 8.37-8.34 (dd, 2H, J=2.2, 11.0), 8.19-8.17 (d, 2H, J=8.8), 7.91-7.89 (d, 1H, J=7.1), 7.61-7.53 (m, 2H), 7.04-7.01 (m, 3H), 6.74-6.72 (dd, 2H, J=2.2, 11.0), 6.53-6.51 (d, 2H, J=8.5).

$^{13}$C-NMR (99.5 MHz, CDCl$_3$/CD$_3$OD) δ 168.97, 151.38, 149.84, 148.06, 137.38, 135.28, 133.07, 130.11, 129.16, 127.12, 126.62, 125.99, 125.10, 123.58, 120.31, 116.52, 115.68, 108.70.

QSTAR(Applied Biosystems/MDS SCIEX)(ESI-Q-TOF): [M–H]-C$_{32}$H$_{17}$N$_6$O$_{15}$S$_2$: calcd. 789.0193. Found 789.0176

Example A1

Fluorescence Measurement (Method)

The reaction was carried out using the 100 nM probe (compound 2) and 10 mM cysteine at 37° C. for 30 minutes in 50 mM Tris-HCl (pH 7.4). A fluorescence spectrum was obtained with a fluorescence spectrometer (FP-6500; JASCO). Fluorescence was obtained by excitation at 490 nm at a scanning range of 450 to 650 nm.

(Results)

In order to examine fluorescence response, the probe (synthesized in Synthesis Example A1) was incubated in a Tris-HCl buffer (50 mM, pH 7.4), with or without cysteine. The obtained absorption spectrum and fluorescence spectrum are shown in FIG. 1. The solution without cysteine exhibited the maximum absorption at 516 nm derived from the DNB group. In a case in which cysteine was added to the probe solution, the maximum absorption peak was shifted to the short wavelength side (498 nm) as a result of the cleavage of the DNB group (FIG. 1a). Fluorescence characteristics were also examined. In the probe without cysteine, no significant fluorescence was observed by excitation at 490 nm. However, after cysteine had been added to the solution, strong fluorescence was generated around 520 nm, and the fluorescence intensity was increased by a factor of approximately 3500 (FIG. 1b).

Example A2

Reactivity of Probe with Thiol (Method)

The reactivity of the probe (compound 2) with several types of thiols was examined by measuring an increase in the fluorescence intensity at 522 nm. The reaction was carried out using the 1 μM probe and 1 mM thiol at 37° C. for 30 minutes in 50 mM Tris-HCl (pH 7.4).

In addition, as a comparative example, a compound represented by the following formula (3) was used as a probe, and its reactivity was examined in the same above manner:

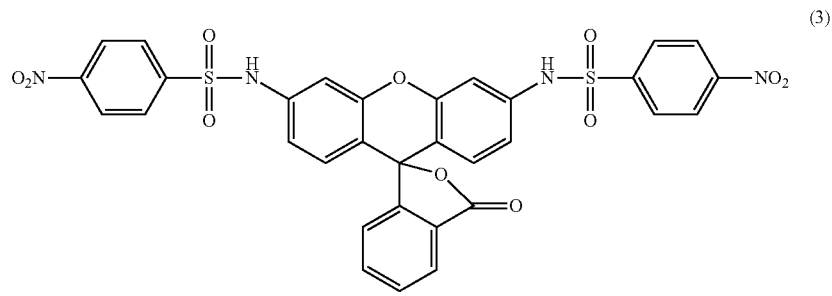

(3)

(Results)

When the present probe is applied to the detection of biological thiol, selectivity is an important issue. The probe should specifically respond to thiol, and it should not generate signals with respect to other biological substances. In order to examine such selectivity, the probe was treated with several biological substances, and fluorescence signals were then measured. The selectivity of the probe to thiol was verified by monitoring the fluorescence at 522 nm using a biologically-relevant substance under physiological conditions. As shown in FIG. 2, a significant increase (50 to 200 times) in the fluorescence intensity was observed in the reaction of the probe with cysteine, phosphorothioate, dithiothreitol, and glutathione. However, in the reaction of the probe with 2-mercaptoethanol (ME), only a slight increase (11 times) in the fluorescence intensity was observed. The pKa value of 2-mercaptoethanol is 9.5, and this is a value higher than those of other types of thiols. Accordingly, the reaction with the DNB group should progress slowly. As is predicted, the probe did not exhibit activity on other biological substances such as glycine, ascorbic acid, or hydrogen peroxide. The present probe was extremely stable in a biological environment. For example, even after the probe had been heated at 55° C. for 24 hours in a 50 mM Tris buffer (pH 7.4), no increase in the fluorescence signal was detected. As described above, it was confirmed that the probe of the present invention exhibits excellent selectivity to biological thiol and that it does not generate an unnecessary fluorescence signal.

Moreover, in the case of the compound represented by the formula (3) used as a comparison, it reacted only with phosphorothioate (approximately 950 times), and it did not react with other thiol groups (FIG. 4).

Example A3

Fluorescence Microscope Observation (Method)

HeLa cells were allowed to grow at 37° C. in a 5% $CO_2$ atmosphere in MEM in order to use them for a test with living cells. The cells were incubated at 37° C. for 15 minutes in the presence of the 25 μM probe (compound 2) (1:100 DMSO/PBS(−), v/v). As a control experiment, the cells were treated with 1 mM N-methylmaleimide in PBS(−) at 37° C. for 60 minutes, and the resultant cells were then washed with a PBS(−) buffer three times. Thereafter, the cells were incubated at 37° C. for 15 minutes in the presence of the 25 μM probe (1:100 DMSO/PBS(−), v/v).

The fluorescence image was obtained using a digital camera (Cool Snap HQ; Roper Scientific) and imaging software (MetaMorph; Molecular Devices), under a fluorescence microscope equipped with a mercury lamp (Axiovert 200M; Carl Zeiss). The conditions of the microscope were determined as follows. Excitation: 470/40 bandpass filter; light emission: 525/50 bandpass filter; and irradiation time: 300 msec.

(Results)

The most important intended use of the probe of the present invention is the monitoring of thiol in living cells. In order to examine the possibility of such intended use, an attempt was made to create an image of the biological thiol existing in the HeLa cells. The results obtained by photographing a brightfield image and a fluorescent image using a fluorescence microscope are shown in FIG. 3. When the cells were incubated together with the probe (25 μM) of the present invention for 15 minutes, the cells exhibited a significant fluorescence signal (FIG. 3d). Such strong signal was localized in the cytoplasm. On the other hand, the nucleus exhibited a weak fluorescence signal. In contrast, in a case in which the cells were pre-treated with N-methylmaleimide used as a thiol-blocking agent and were then incubated with the probe of the present invention in the same above manner, no fluorescence signal was observed (FIG. 3b). These results demonstrated that the probe of the present invention permeates into the cell membrane, and that it is able to perform imaging of a change in the thiol level in living cells. That is to say, the fluorescent probe of the present invention is able to generate a signal in response to thiol, and thus it can be applied to the imaging of biological thiol existing in living cells.

Example B

Synthesis Example B1: Synthesis of the probe of the present invention

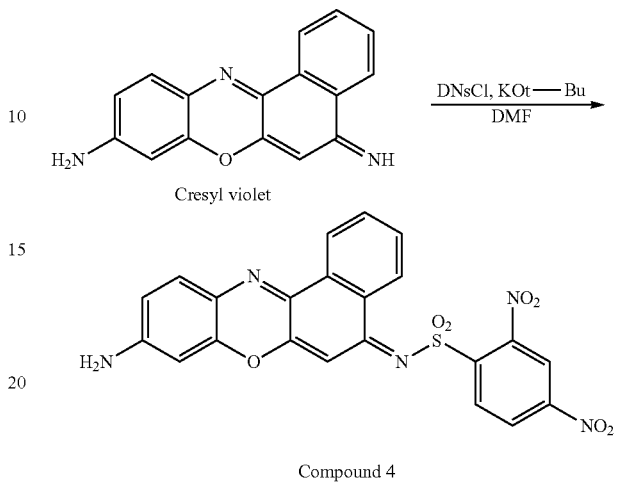

Compound 4

Cresyl violet (250 mg, 0.691 mmol) was dissolved in 7 mL of DMF, and the obtained solution was then cooled on ice. KOt-Bu (155 mg, 1.38 mmol) dissolved in 1 mL of THF was added dropwise to the reaction solution, and the mixed solution was then stirred in an argon atmosphere for 1 hour. Thereafter, $ClSO_2Ph(NO_2)_2$ (368 mmol, 1.38 mmol) was added to the reaction solution, and the mixture was then stirred for 1 hour. Subsequently, the reaction solution was diluted with ethyl acetate, followed by liquid separation using a saturated sodium bicarbonate solution and water. The organic layer was washed with a saturated saline, and was then dried over anhydrous sodium sulfate. Thereafter, the solvent was removed by distillation under reduced pressure. The residue was purified by silica gel column chromatography, so as to obtain a compound 4 of interest (30 mg, 0.061 mmol, 9%).

$^1$H-NMR (300 MHz, DMSO): δ8.85-8.84 (1H, d, J=1.3 Hz, Ar), 8.71-8.69 (1H, d, J=8.0 Hz, Ar) 8.60-8.57 (1H, d, J=10.6 Hz, Ar) 8.45-8.43 (1H, d, J=8.76 Hz, Ar) 8.36-8.34 (1H, d, J=8.1 Hz, Ar) 7.89-7.71 (5H, m, Ar) 7.19 (1H, s, Ar) 7.03-7.00 (1H, d, J=11.0 Hz, Ar) 6.76-6.75 (1H, d, J=2.2 Hz, Ar)

$^{13}$C-NMR (99.5 MHz, DMSO): δ174.22, 163.10, 158.89, 151.77, 150.20, 148.64, 147.27, 139.76, 133.99, 133.22, 131.75, 131.45, 130.48, 129.40, 127.26, 125.50, 123.44, 122.66, 120.03, 117.49, 99.42, 97.17

QSTAR(Applied Biosystems/MDS SCIEX)(ESI-Q-TOF): [M+H]+ $C_{22}H_{14}IN_5O_7S$: calcd. 492.0608. Found 492.0604.

Example B1

Fluorescence Measurement in Solution (Method)

The 100 nM probe (compound 4) was allowed to react with 10 mM GSH in 50 mM Tris-HCl (pH 7.4) at 37° C. for 30 minutes. Thereafter, the fluorescence intensity was measured using a fluorescence spectrometer (FP-6500; JASCO) (excitation wavelength: 540 nm).

(Results)

The fluorescence characteristics of the synthesized probe (compound 4) were analyzed by reacting the probe with GSH (Glutathione). The fluorescence spectrum was measured with an excitation light of 540 nm. As a result, DNs-CV as a single body generated no fluorescence, but the DNs group was deprotected by reacting the DNs-CV with GSH, and thereby an increase in the fluorescence intensity was observed at 620 nm (FIG. 5).

Example B2

Flow Cytometry (Method)

The 100 μM probe (compound 4) was added to HL60, and the mixture was then reacted at 37° C. for 15 minutes. Thereafter, a measurement was then carried out by flow cytometry. 1 mM N-methylmaleimide (N-MMI) used as a thiol-blocking agent was added to HL60, and the obtained mixture was then reacted at 37° C. for 30 minutes. Thereafter, the 100 μM probe was added to the reaction product, and the obtained mixture was reacted at 37° C. for 15 minutes. Thereafter, the measurement was carried out by flow cytometry.

(Results)

The results obtained by making an attempt to quantify GSH in living cells using DNs-CV by flow cytometry are shown in FIG. 6. The HL60 cells (−N-MMI), into which DNs-CV had been merely introduced, had a fluorescence intensity higher than that of the HL60 cells (+N-MMI), which had been treated with N-methylmaleimide (N-MMI) used as a GSH-blocking agent and into which DNs-CV had been then introduced. The present probe (compound 4) enabled a quantitative measurement. These results shows that DNs-CV selectively reacts with GSH in living cells, so as to generate fluorescence. The above-mentioned results demonstrated that a novel fluorescent compound DNs-CV is a useful agent for detecting GSH activity in cells.

BRIEF DESCRIPTION OF THE DRAWINGS

FIG. 1a shows the absorption spectrum of a 20 μM probe in 50 mM Tris-HCl (pH 7.4) with 20 mM Cys (solid line) and without 20 mM Cys (dotted line). FIG. 1b shows the fluorescence spectrum of a 100 nM probe with 10 mM Cys (solid line) and without 10 mM Cys (dotted line), after completion of the incubation in 50 mM Tris-HCl (pH 7.4) at 37° C. for 30 minutes. Fluorescence was monitored by excitation at 490 nm.

FIG. 2 shows the fluorescence intensity of a 1 μM probe in 50 mM Tris-HCl (pH 7.4) in the presence of 1 mM thiol. After addition of thiol, the solution was incubated at 37° C. for 30 minutes. The fluorescence at 522 nm was monitored by excitation at 490 nm. "3'-thio dT" indicates 3'-phosphorothioate-2'-deoxythymidine; "DTT" indicates dithiothreitol; "GSH" indicates glutathione; "L-Gly" indicates L-glycine; and "Vc" indicates ascorbic acid.

FIG. 3 shows the fluorescent image of HeLa cells. (a, b): a control image of the cells, which were pre-treated with N-methylmaleimide (1 mM) at 37° C. for 60 minutes and were then incubated together with the probe (25 μM) at 37° C. for 15 minutes; (c, d): an image of the cells, which were incubated together with the probe (25 μM) at 37° C. for 15 minutes; (a, c) a bright-field image; (b, d) a fluorescent image. The conditions of the microscope were determined as follows. Excitation: 470/40 bandpass filter; light emission: 525/50 bandpass filter; and irradiation time: 300 msec.

FIG. 4 shows the fluorescence intensity of a 1 μM probe (a compound as a comparison) in 50 mM Tris-HCl (pH 7.4) in the presence of 1 mM thiol. After addition of thiol, the solution was incubated at 37° C. for 30 minutes. The fluorescence at 522 nm was monitored by excitation at 490 nm. "3'-thio dT" indicates 3'-phosphorothioate-2'-deoxythymidine; "DTT" indicates dithiothreitol; "GSH" indicates glutathione; "L-Gly" indicates L-glycine; and "Vc" indicates ascorbic acid.

FIG. 5 shows the results obtained by reacting the 100 nM probe (compound 4) with 10 mM GSH in 50 mM Tris-HCl (pH 7.4) at 37° C. for 30 minutes and then carrying out a measurement using a fluorescence spectrometer (excitation wavelength: 540 nm).

FIG. 6 shows the results obtained by adding the 100 μM probe (compound 4) to HL60, reacting the mixture at 37° C. for 15 minutes, and then carrying out a measurement by flow cytometry.

The invention claimed is:

1. A compound represented by the following formula (1):

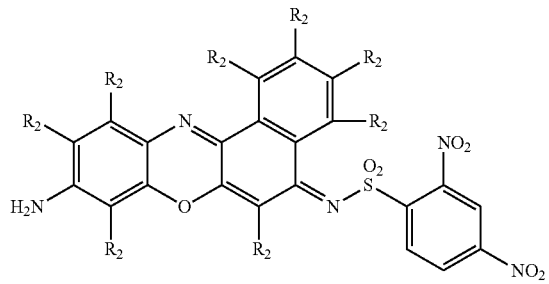

(1)

wherein each $R_2$ independently represents an alkyl group containing 1 to 6 carbon atoms, a halogen atom, or a hydrogen atom.

2. A compound represented by the following formula (1A):

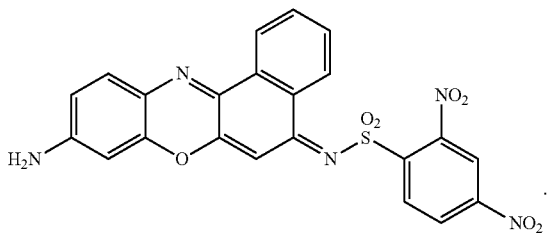

(1A)

3. A thiol-detecting reagent which comprises the compound of any one of claims 1 to 2.

4. A method for detecting thiol, which comprises detecting fluorescence which is generated by allowing the compound of claim 1 to react with a compound having a thiol group.

5. The method for detecting thiol according to claim 4, wherein the reaction with the compound having a thiol group is carried out in a cell.

6. The method for detecting thiol according to claim 4, wherein the compound having a thiol group is a biomolecule.

* * * * *